US00PP31046P2

(12) United States Plant Patent
Heimovaara

(10) Patent No.: US PP31,046 P2
(45) Date of Patent: Nov. 12, 2019

(54) ***CHRYSANTHEMUM* PLANT NAMED 'ZANMUWILD'**

(50) Latin Name: ***Chrysanthemum* x *morifolium* Ramat.**
Varietal Denomination: Zanmuwild

(71) Applicant: Van Zanten Breeding BV, Aalsmeer (NL)

(72) Inventor: Sjoukje Heimovaara, Valkenburg (NL)

(73) Assignee: VAN ZANTEN BREEDING BV (NL)

( * ) Notice: Subject to any disclaimer, the term of this patent is extended or adjusted under 35 U.S.C. 154(b) by 0 days.

(21) Appl. No.: 16/350,569

(22) Filed: Dec. 4, 2018

(51) Int. Cl.
*A01H 5/02* (2018.01)
*A01H 6/14* (2018.01)

(52) U.S. Cl.
USPC ..... Plt./287

(58) Field of Classification Search
USPC ..... Plt./263.1, 284, 286, 287
See application file for complete search history.

*Primary Examiner* — Susan McCormick Ewoldt
*Assistant Examiner* — Karen M Redden
(74) *Attorney, Agent, or Firm* — Steptoe & Johnson LLP

(57) ABSTRACT

A *chrysanthemum* plant named 'Zanmuwild' characterized by its medium sized blooms with pink ray florets and prolific branching; natural season flowering date September 10, blooming for a period of 5 weeks.

2 Drawing Sheets

Botanical designation: *Chrysanthemum* x *morifolium* Ramat.

Cultivar denomination: 'Zanmuwild'.

RELATED CULTIVARS

This new plant cultivar 'Zanmuwild' is of the botanical classification *Chrysanthemum* x *morifolium* Ramat.

BACKGROUND OF THE INVENTION

The present invention relates to a new and distinct cultivar of *chrysanthemum* plant, botanically known as *Chrysanthemum* x *morifolium* Ramat., commercially known as a garden mum, and hereinafter referred to by the cultivar denomination 'Zanmuwild'. 'Zanmuwild' is a product of a breeding and selection program for outdoor pot mums (garden mums) which had the objective of creating new cultivars with a double type inflorescence, a natural season flowering date around September 10, blooming for a period of 5 weeks. 'Zanmuwild' is a seedling resulting from a cross of the female parent 55335 (unpatented) with the male parent 55865 (unpatented). Plants of the new cultivar 'Zanmuwild' differ from plants of the female parent in the plant vigor: plants of the female parent are less vigorous than those of the seedling. Plants of the new cultivar 'Zanmuwild' differ from plants of the male parent in the following characteristics: (1) Plant habit, and (2) Natural season flowering date. (1) Plants of the male parent show a more spreading plant habit than those of the seeding. (2) Plants of the male parent flower earlier in autumn than those of the seedling.

The new and distinct cultivar was discovered and selected as a flowering plant by Sjoukje Heimovaara on a cultivated field in Rijsenhout, the Netherlands in August 2012. The first act of asexual production of 'Zanmuwild' was accomplished when vegetative cuttings from the initial selection were propagated further in a controlled environment in September 2012, in Rijsenhout, the Netherlands. In summer, about 6-8 days are needed to initiate roots in cuttings of the new cultivar, after another 5 days rooted plants are formed. The new cultivar has been found to retain its distinctive characteristics through successive propagations.

BRIEF DESCRIPTION OF THE DRAWINGS

The present invention of a new and distinct variety of *chrysanthemum* (of about 15 weeks) is shown in the accompanying drawings, the color being as nearly true as possible with color photographs of this type.

DESCRIPTION OF THE INVENTION

Figure 1:
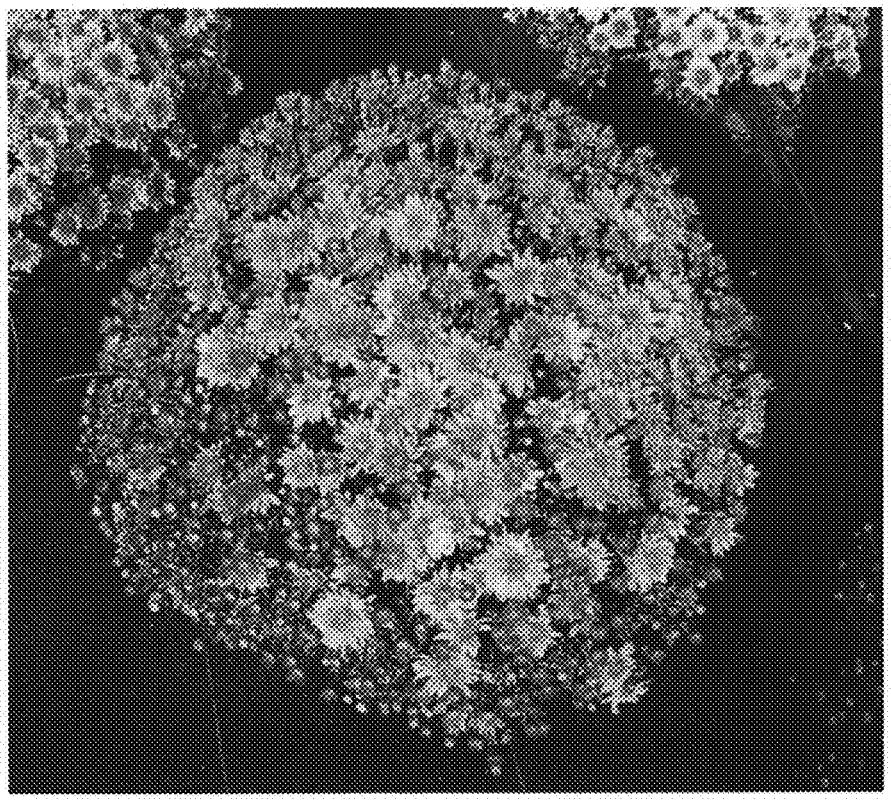
FIG. 1 shows a plant of the new cultivar in full bloom.
Figure 2:
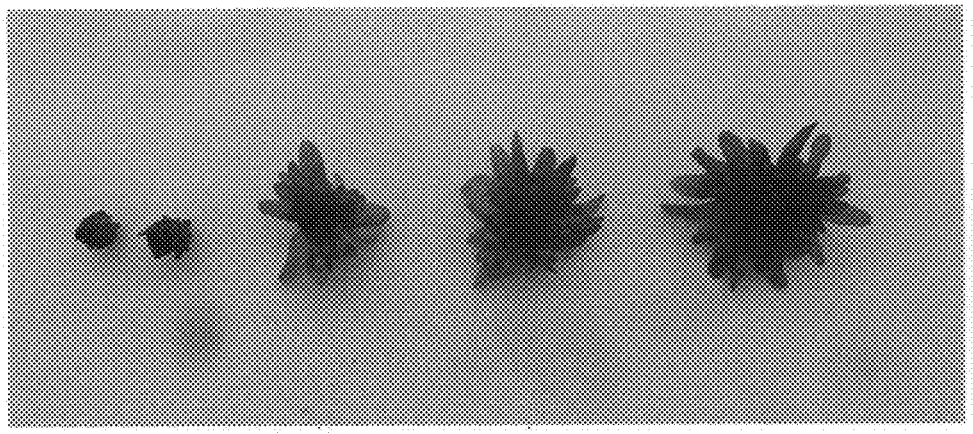
FIG. 2 shows the various stages of bloom of the new cultivar.
Figure 3:
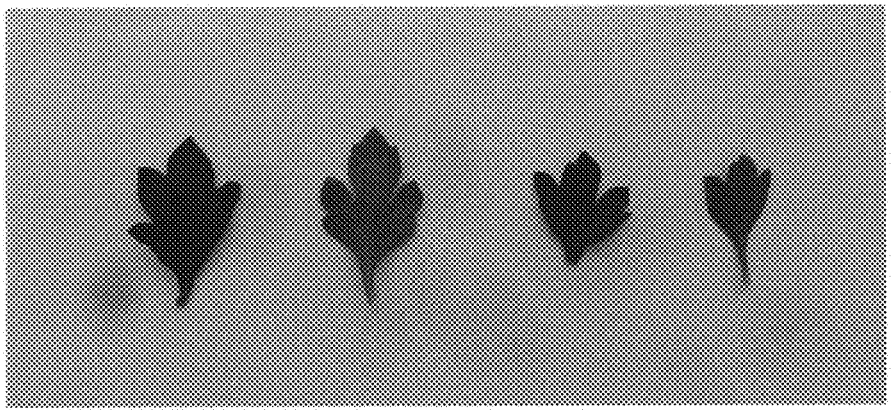
FIG. 3 shows the various stages of foliage of the new cultivar.

The observations and measurements were gathered from plants in the period of 13 to 19 weeks of age grown outdoor in Rijsenhout, the Netherlands, under natural day length and temperature and planted in week 21 in 2018, receiving drip irrigation. The natural blooming date of this crop was September 10 (week 37). The average height of the plants was 36 cm. No growth retardants were used. No tests were done on disease or insect resistance or susceptibility. No tests were done on cold or drought tolerance. This new variety produces medium sized pink blooms with dark centers for a period of 5 weeks.

From the cultivars known to the inventor the most similar existing cultivar in comparison to 'Zanmuwild' is 'Zanmuflamin' (U.S. Plant Pat. No. 20,589). When 'Zanmuflamin' and 'Zanmuwild' are compared the following differences are noticed: (1) Natural season flowering date, and (2) Inflorescence size. (1) Plants of 'Zanmuflamin' flower later in the season than those of 'Zanmuwild'. (2) Inflorescences of 'Zanmuflamin' are smaller than those of 'Zanmuwild'.

The following is a description of the plant and characteristics that distinguish 'Zanmuwild' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, sixth edition (2015).

Botanical Description of *Chrysanthemum* x *morifolium* Ramat. 'Zanmuwild'

Bud:
- *Size*.—Small; cross-section 7 mm, height 6 mm.
- *Shape*.—Round.
- *Texture*.—Pubescent.
- *Outside color*.—Green 138B.

Phyllaries:
- *Number*.—18, arranged in 3 rows.
- *Shape*.—Elliptic.
- *Apex*.—Acute.
- *Base*.—Truncate.
- *Margin*.—Entire.
- *Color*.—Upper side: Green NN137B. Lower side: Green N138B.
- *Length and width*.—7 mm; 1.5 mm.
- *Texture*.—Pubescent.

Inflorescences:
- *Type*.—Double.
- *Height*.—1.8 cm.
- *Diameter*.—5.5-6 cm.
- *Peduncle length*.—7-9 cm.
- *Peduncle color*.—Green N138D.
- *Peduncle diameter*.—1.5 mm.
- *Peduncle texture*.—Pubescent.
- *Number per branch*.—About. 6-7 inflorescences.
- *Duration of flowering*.—5 weeks.
- *Seeds*.—Produced in small quantities, ovate, Greyed-brown 199A, length 1.5 mm, diameter 0.5 mm; texture: rough with ribs.
- *Fragrance*.—Faint *chrysanthemum* odor.

Color inflorescences:
- *Center of inflorescence*.—Immature stage: Greyed-Purple N186D; Mature stage: Greyed-Purple N186D.
- *Color of upper side of ray florets*.—Outer rows: Greyed-purple 186B; Inner Rows: Greyed-purple 186D.
- *Color of lower side of ray florets*.—Outer rows: Greyed-purple 186C; Inner rows: Greyed-purple 186D.
- *Tonality from distance*.—A garden mum with pink blooms having a dark center.
- *Color of ray florets after aging of the plant*.—Greyed-purple 186D.

Ray florets:
- *Number of types*.—2.
- *Type*.—Ligulate.
- *Number of rows*.—Outer: 8; Inner: 5.
- *Texture*.—Upper and lower side smooth.
- *Number*.—Outer rows: about 160; Inner rows: about 70.
- *Shape*.—Outer rows: Elliptic; Inner rows: Narrowly elliptic.
- *Apex*.—Rounded.
- *Base*.—Attenuate.
- *Cross-section*.—Outer rows: Flat; Inner rows: Strongly concave.
- *Longitudinal axis*.—Outer rows: Straight; Inner rows: Incurving.
- *Length of corolla tube*.—3 mm.
- *Diameter corolla tube*.—1 mm.
- *Ray floret margin*.—Entire.
- *Ray floret length*.—Outer rows: 1.5-2.2 cm: Inner rows: 1.2 cm.
- *Ray-floret width*.—Outer rows: 4-6 mm; Inner rows: 1-2 mm.
- *Ratio length/width*.—Medium.

Disc florets:
- *Disc diameter*.—2 mm.
- *Distribution of disc florets*.—Few, only visible in mature stage of inflorescences.
- *Shape*.—Domed raised.
- *Color*.—Yellow-green 145C at base to Green Yellow 11D at apex.
- *Length*.—3 mm.
- *Diameter*.—1 mm.

Receptacle:
- *Color*.—Green 138D.
- *Shape*.—Domed raised.
- *Height*.—5 mm.
- *Diameter*.—3 mm.

Reproductive organs:
- *Androecium*.—Present on only disc florets.
- *Stamen length*.—3 mm.
- *Stamen color*.—Yellow-green 144A.
- *Anther color*.—Yellow 2A.
- *Pollen*.—Scarce.
- *Pollen color*.—Yellow 12A.
- *Gynoecium*.—Present on both ray and disc florets.
- *Style color*.—Yellow-green 154C.
- *Style length*.—4 mm.
- *Stigma color*.—Yellow 7A.
- *Stigma width*.—1 mm.
- *Ovary*.—Enclosed in calyx.
- *Ovary color*.—Yellow-green 149D.

Plant:
- *Type*.—Bushy.
- *Growth habit*.—Spherical shape.
- *Growth rate*.—Medium.
- *Height*.—36 cm.
- *Width*.—45-50 cm.
- *Stem color*.—Greyed-brown 199A.
- *Stem strength*.—Not strong.
- *Stem brittleness*.—Brittle.
- *Stem anthocyanin coloration*.—Absent.
- *Internode length*.—2-2.5 cm.
- *Length of lateral branch*.—From top to bottom 15-20 cm.
- *Lateral branch color*.—Green 137 D.
- *Lateral branch, attachment*.—Weak.
- *Lateral branch diameter*.—1.5 mm.
- *Lateral branch, texture*.—Pubescent with ribs.
- *Branching (average number of lateral branches)*.—Dense with 8 breaks after pinching.
- *Natural season blooming date*.—September 10 (week 37) in Rijsenhout, the Netherlands.
- *Roots*.—Habits: Fine, freely branching.
- *Roots*.—Color: White 155A.

Foliage:

*Glossiness*.—Leaf upper side: weak. Leaf lower side: weak.

*Leaf color*.—Upper side: Green NN137A. Lower side: Green 138B.

*Color midvein*.—Upper side: Yellow-green 147D. Lower side: Yellow-green 148D.

*Size*.—Small; length 2-3.5 cm, width 2-2.2 cm.

*Quantity* (*number per lateral branches*).—20-24.

*Shape*.—Broad elliptic.

*Texture upper side*.—Sparsely pubescent.

*Texture under side*.—Pubescent.

*Venation arrangement*.—Pinnate.

*Shape of margin*.—Serrated.

*Shape of base of sinus between lateral lobes*.—Rounded.

*Margin of sinus between lateral lobes*.—Diverging.

*Shape of base*.—Truncate to asymmetric.

*Apex*.—Mucronulate.

*Petiole strength*.—Weak.

*Petiole attitude*.—Upwards.

*Petiole length*.—0.8 cm.

*Petiole diameter*.—2 mm.

*Petiole color*.—Yellow-green 147D.

*Stipules*.—Absent.

Differences with the comparison variety, when grown under identical conditions

| | 'Zanmuwild' | 'Zanmuflamin' |
|---|---|---|
| Natural season flowering date | Week 37 | Week 38 |
| Inflorescence size | 5.5-6 cm | 5 cm |

I claim:

1. A new and distinct *chrysanthemum* plant named 'Zanmuwild' as described and illustrated.

* * * * *